(12) United States Patent
Rakhorst et al.

(10) Patent No.: US 7,988,655 B2
(45) Date of Patent: *Aug. 2, 2011

(54) CATHETER PUMP, CATHETER AND FITTINGS THEREFORE AND METHODS OF USING A CATHETER PUMP

(75) Inventors: Gerhard Rakhorst, Groningen (NL); Jan-Paul Van Loon, Groningen (NL); Martijn John Van Der Bom, Castricum (NL)

(73) Assignee: Pulsecath B.V., Amsterdam (NL)

( * ) Notice: Subject to any disclaimer, the term of this patent is extended or adjusted under 35 U.S.C. 154(b) by 197 days.

This patent is subject to a terminal disclaimer.

(21) Appl. No.: 12/351,329

(22) Filed: Jan. 9, 2009

(65) Prior Publication Data

US 2009/0149695 A1 Jun. 11, 2009

Related U.S. Application Data

(63) Continuation of application No. 10/931,381, filed on Sep. 1, 2004, now Pat. No. 7,494,477.

(60) Provisional application No. 60/499,488, filed on Sep. 2, 2003.

(51) Int. Cl.
*A61M 37/00* (2006.01)
*A61M 25/00* (2006.01)
(52) U.S. Cl. ............... 604/6.05; 600/16; 604/532
(58) Field of Classification Search ............... 604/6.05, 604/532; 600/16
See application file for complete search history.

(56) References Cited

U.S. PATENT DOCUMENTS

| 55,355 A | 6/1866 | Parsons |
| 758,643 A | 5/1904 | Haigh |
| 1,029,689 A | 6/1912 | Kelley |
| 1,242,806 A | 10/1917 | Hohein |
| 1,666,197 A | 4/1928 | Dolmatch |
| 1,728,542 A | 9/1929 | Hames |
| 3,176,690 A | 4/1965 | Doubler |
| 3,411,502 A | 11/1968 | Hofstra et al. |
| 3,513,845 A | 5/1970 | Callaghan et al. |
| 3,583,404 A | 6/1971 | McWhorter |

(Continued)

FOREIGN PATENT DOCUMENTS

EP 0268733 A2 6/1988

(Continued)

OTHER PUBLICATIONS

Allen, et al.; "The Importance of Pulsatile and Nonpulsatile Flow in the Design of Blood Pumps"; Artificial Organs 1997; 21(8): 922-928.

(Continued)

*Primary Examiner* — Jacqueline F Stephens
*Assistant Examiner* — Paula Craig
(74) *Attorney, Agent, or Firm* — Pearne & Gordon LLP

(57) ABSTRACT

A catheter pump includes a catheter channel communicating with a distal end portion of the catheter for alternatingly leading fluid in proximal and distal directions. At least one outlet passage is distally spaced from the inlet passage or passages. The catheter pump further includes a displacement structure communicating with the proximal end portion of the catheter for alternatingly applying suction and pressure for driving the fluid displacement. At least in operating condition, the inlet passage or passages are continuously open. A catheter and fittings for such a catheter pump and method of using a catheter pump are also described.

11 Claims, 7 Drawing Sheets

U.S. PATENT DOCUMENTS

| | | | |
|---|---|---|---|
| 3,592,183 A | | 7/1971 | Watkins et al. |
| 3,592,184 A | * | 7/1971 | Watkins et al. ............... 604/192 |
| 3,599,244 A | * | 8/1971 | Wortman ...................... 623/3.13 |
| 3,753,439 A | | 8/1973 | Brugarolas et al. |
| 3,756,234 A | | 9/1973 | Kopp |
| 3,908,664 A | | 9/1975 | Loseff |
| 3,995,617 A | | 12/1976 | Watkins et al. |
| 4,014,317 A | | 3/1977 | Bruno |
| 4,086,665 A | | 5/1978 | Poirier |
| 4,122,858 A | | 10/1978 | Schiff |
| 4,173,981 A | | 11/1979 | Mortensen |
| 4,230,110 A | | 10/1980 | Beroff |
| 4,250,872 A | | 2/1981 | Tamari |
| 4,318,401 A | | 3/1982 | Zimmerman |
| 4,490,134 A | * | 12/1984 | Troutner ...................... 604/6.05 |
| 4,675,004 A | | 6/1987 | Hadford et al. |
| 4,740,203 A | | 4/1988 | Hoskins et al. |
| 4,754,752 A | | 7/1988 | Ginsburg et al. |
| 4,906,229 A | | 3/1990 | Wampler |
| 4,919,647 A | * | 4/1990 | Nash ............................... 600/16 |
| 4,955,856 A | * | 9/1990 | Phillips ........................... 600/16 |
| 4,964,864 A | * | 10/1990 | Summers et al. ............ 623/3.15 |
| 4,985,014 A | | 1/1991 | Orejola |
| 5,006,111 A | | 4/1991 | Inokuchi et al. |
| 5,053,023 A | | 10/1991 | Martin |
| 5,066,282 A | | 11/1991 | Wijay et al. |
| 5,082,005 A | | 1/1992 | Kaldany |
| 5,147,388 A | * | 9/1992 | Yamazaki ..................... 623/3.13 |
| 5,300,022 A | | 4/1994 | Klapper et al. |
| 5,554,136 A | | 9/1996 | Luther |
| 5,618,270 A | | 4/1997 | Orejola |
| 5,776,190 A | * | 7/1998 | Jarvik ............................. 600/16 |
| 5,785,694 A | | 7/1998 | Cohen et al. |
| 5,807,349 A | | 9/1998 | Person et al. |
| 5,895,376 A | | 4/1999 | Schwartz et al. |
| 5,957,962 A | | 9/1999 | Wallstein et al. |
| 5,984,903 A | | 11/1999 | Nadal |
| 6,007,479 A | | 12/1999 | Rottenberg et al. |
| 6,030,336 A | | 2/2000 | Franchi |
| 6,132,364 A | | 10/2000 | Rottenberg et al. |
| 6,228,063 B1 | | 5/2001 | Aboul-Hosn |
| 6,280,788 B1 | | 8/2001 | Rakhorst et al. |
| 6,338,727 B1 | | 1/2002 | Noda et al. |
| 6,340,355 B1 | | 1/2002 | Barrett |
| 6,398,714 B1 | | 6/2002 | Rakhorst et al. |
| 6,398,717 B1 | | 6/2002 | Leysieffer et al. |
| 6,464,662 B1 | | 10/2002 | Raghavan et al. |
| 6,540,714 B1 | | 4/2003 | Quinn |
| 6,626,859 B2 | | 9/2003 | von Segesser |
| 6,790,196 B2 | | 9/2004 | Kokate et al. |
| 6,887,220 B2 | | 5/2005 | Hogendijk |
| 6,974,409 B2 | | 12/2005 | Verkerke et al. |
| 6,976,996 B1 | | 12/2005 | Aboul-Hosn |
| 7,347,852 B2 | | 3/2008 | Hobbs et al. |
| 7,494,477 B2 | * | 2/2009 | Rakhorst et al. ............. 604/6.05 |
| 2002/0045795 A1 | * | 4/2002 | Aboul-Hosn et al. .......... 600/16 |
| 2002/0072698 A1 | | 6/2002 | Chiang et al. |
| 2002/0123661 A1 | | 9/2002 | Verkerke et al. |
| 2002/0165426 A1 | | 11/2002 | Sporer et al. |
| 2003/0004456 A1 | | 1/2003 | Saab et al. |
| 2003/0187322 A1 | * | 10/2003 | Siess ............................... 600/16 |
| 2003/0225379 A1 | | 12/2003 | Schaffer et al. |
| 2005/0004503 A1 | | 1/2005 | Samson et al. |

FOREIGN PATENT DOCUMENTS

| | | |
|---|---|---|
| FR | 2144806 A1 | 2/1973 |
| GB | 1370546 A | 10/1974 |
| GB | 1528072 A | 10/1978 |
| WO | 8910763 A1 | 11/1989 |
| WO | 9702850 A1 | 1/1997 |
| WO | 9718936 A1 | 5/1997 |
| WO | 9857698 A1 | 12/1998 |
| WO | 9926676 A1 | 6/1999 |
| WO | 9926677 A1 | 6/1999 |
| WO | 0013736 A1 | 3/2000 |
| WO | 0137923 A1 | 5/2001 |

OTHER PUBLICATIONS

Lodge, et al.; "Regional Blood Flow During Pulsatile Cardiopulmonary Bypass and After Circulatory Arrest in an Infant Model"; Ann Thorac Surg 1997; 63:1243-1250.

Sezai, et al.; "Major Organ Function Under Mechanical Support: Comparative Studies of Pulsatile and Nonpulsatile Circulation"; Artificial Organs 1999; 23(3), 280-285.

Undar, et al.; "Effects of Perfusion Mode on Regional and Global Organ Blood Flow in a Neonatal Piglet Model"; Ann Thorac Surg 1999; 68:1336-1343.

Orime, et al.; "Cytokine and Endothelial Damage in Pulsatile and Nonpulsatile Cardiopulmonary Bypass"; Artificial Organs 1999; 23(6): 508-512.

Catheter, 2006, Churchill Livingstone's Dictionary of Nursing, CredoReference, 1 page.

\* cited by examiner

CATHETER PUMP, CATHETER AND FITTINGS THEREFORE AND METHODS OF USING A CATHETER PUMP

This application claims the benefit of U.S. Provisional Patent Application Ser. No. 60/499,488 filed on Sep. 2, 2003.
This application claims the benefit of U.S. patent application Ser. No. 10/931,381 filed Sep. 1, 2004, now U.S. Pat. No. 7,494,477.

TECHNICAL FIELD

The invention relates to a catheter pump, to a catheter, to fittings therefore and to a method of using a catheter pump.

BACKGROUND ART

From U.K. patent specification 1,370,546 a heart assist catheter pump is known which includes a catheter having a distal end for insertion from the aorta past the aortic valve into the left ventricle. The distal end has inlet openings. Spaced from the distal end, the catheter has outlet openings and a set of check valves for allowing outward flow. Valves are provided for controlling the direction of the flow. A fluid displacement device communicating with the proximal end of the catheter alternatingly generates a suction causing blood to be withdrawn from the left ventricle into the catheter and to the displacement device and an excess pressure causing blood to be expelled from the catheter downstream side of the aortic valve.

Later catheter pumps for assisting the left ventricle heart by pumping blood from a distal catheter tip portion to an outlet spaced from the distal tip are disclosed in U.S. Pat. Nos. 3,995,617, 4,014,317, 6,007,479 and 6,398,714. U.S. patent application 2002/0123661 discloses the use of a catheter pump with an inlet distally from the outlet for causing blood pressure pulsations in the aorta, for instance in addition to a non-pulsatile flow maintained by a heart lung machine.

However, for some clinical applications, blood is pumped through the catheter in opposite direction, i.e. from an inlet in a position spaced from the distal tip towards the distal tip.

One example of such a clinical application is assisting the function of the right ventricle of the heart. Devices for assisting this function are known as Right Ventricular Assist Devices (RVAD). An example of a RVAD in the form of catheter pump is disclosed in U.S. Pat. No. 4,985,014 in which the catheter is a double lumen or coaxial channel catheter and the pump a roller pump. Examples of single lumen catheter pumps for use as a RVAD are disclosed in International patent applications WO99/26677 and WO00/13736.

Another example of a clinical application in which blood is pumped from an inlet in a position spaced from the distal tip to the distal tip is proposed in International patent application WO99/26676. According to this document, the catheter is inserted through an incision in the left ventricle and advanced until the distal end is in the aorta while a more proximal portion including an inlet is in the left ventricle. The catheter then functions as a left ventricular assist device.

An important problem associated with pumping blood is that blood cells are easily damaged in the valves, where the blood experiences abrupt changes in either the rate or direction of its flow under influence of mechanical forces and that, at the valves, the risk of thrombosis is increased. In International patent application WO 98/57698, the problem of blood cell damage is addressed and special valves are proposed. U.S. Pat. No. 6,398,714 discloses to reduce the risk of thrombosis by providing a single valve that alternatingly closes off a passage in the wall of the catheter and the lumen of the catheter. However, these solutions are still relatively complex and specifically suitable for catheters in which blood is displaced away from the tip towards an outlet more spaced from the tip than the inlet.

SUMMARY OF THE INVENTION

It is an object of the present invention to provide a simple and reliable catheter pump of the type in which blood is alternatingly displaced towards and away from a proximal displacement structure and, generally, moves from an inlet spaced from the tip to a more distal outlet, in which the risk of blood damage and thrombosis is at least reduced.

According to the invention, this object is achieved by providing a catheter pump including a catheter, the catheter including:
  a catheter wall bounding a channel inside the catheter,
  a distal end portion;
  a proximal end portion, the channel communicating with the distal end portion for alternatingly leading fluid in the channel in a direction away from the distal end portion towards the proximal end portion and in a direction away from the proximal end portion towards the distal end portion;
  at least one inlet passage in the wall; and
  at least one outlet passage distally spaced from the inlet passage.

The catheter pump further includes a displacement structure communicating with the proximal end portion of the catheter for alternatingly applying suction and pressure for driving the fluid displacement. At least in operating condition, the at least one inlet passage is continuously open.

The invention can also be embodied in a catheter as set fort above adapted to form a catheter pump in combination with a displacement device communicating with the proximal end of the catheter.

The invention can further be embodied in fitting for a catheter pump according to the invention.

According to one aspect of the invention such a fitting is adapted for forming the inlet passages of the catheter pump and, to that end, includes a tubular section having a wall bounding a channel, at least one inlet passage in the wall, wherein, at least in operating condition, the at least one inlet passage is continuously open.

According to another aspect of the invention such a fitting is adapted for providing a check valve of a catheter pump according to a particular embodiment of the invention and, to that end, includes a tubular section bounding a channel, a valve located in the channel, the valve including a valve body pivotably suspended for rotation about an axis extending across the channel, between a closed position, substantially closing off the channel and an open position allowing fluid to pass past the valve, wherein the valve body in open position extends along a plane parallel to the channel, in axial view, has a central portion spaced from the pivoting axis and, in side view, projecting from the pivoting axis further in distal direction than in proximal direction.

In spite of the inlet passage or passages being continuously open, when the displacement device alternatingly urges blood through the channel in distal and proximal direction, over a complete cycle, a net displacement of blood from the inlet through the channel to the outlet is obtained. If any, the volume of blood that is pushed back through the inlet opening or openings when the displacement device displaces blood in distal direction is smaller than the volume of blood that enters the channel via the inlet opening or openings when blood is pulled through the catheter channel in proximal direction. This effect is achieved because during flow in distal direction, blood reaches the inlet passages as a flow having a direction determined by the direction in which the channel extends immediately proximally of the inlet passage or passages, i.e. the flow in distal direction has a substantial directional effect on the flow in the area of the inlet passage or passages. In contrast, the direction of the flow in proximal direction away from the inlet passage or passages has relatively little directional effect on the flow in the area of the inlet passage or passages. Therefore, in response to the withdrawal of blood from behind the inlet passage or passages, blood can flow into the channel via the inlet passage or passages in directions having a component transverse to the direction of the channel via the inlet relatively easily.

Since, in operation, the inlet passage or passages are continuously open, there is no need to provide valves at the inlet passage or passages. In turn, this allows a very simple construction and blood cell damage and risk of thrombosis as typically caused by valves are avoided.

The catheter pump and the catheter according to the invention are very suitable for carrying out a method according to the invention in which pulsations in the blood flow towards the organs of a patient are generated. In this method, a catheter is inserted into the aorta via an incision in the aorta or via an arm or breast area and a subclavian artery, and brought in a position having a distal end portion in the aorta of the patient. Then, alternatingly, fluid is withdrawn from a first area and fed to a second area located in the aorta and downstream of the first area, via the catheter, such that pressure pulsations are generated in an area of the aorta where the distal end portion of the catheter is located.

The catheter is thus arranged in the aorta with its distal end portion oriented in downstream direction with the fluid inlet located proximally of the fluid outlet. Withdrawing the fluid from an area upstream of the section of the aorta where the fluid is expelled from the catheter is relatively easy and the pulsatile outflow in the narrower section of the aorta is very effective for causing pulsatile pressure peaks of the blood pressure in a section of the aorta where the arteries towards the organs branch off from the aorta.

Particular embodiments of the invention are set forth in the dependent claims.

Further objects, features, effects, advantages and details of the invention are described with reference to examples shown in the drawings.

DETAILED DESCRIPTION

Figure 1:
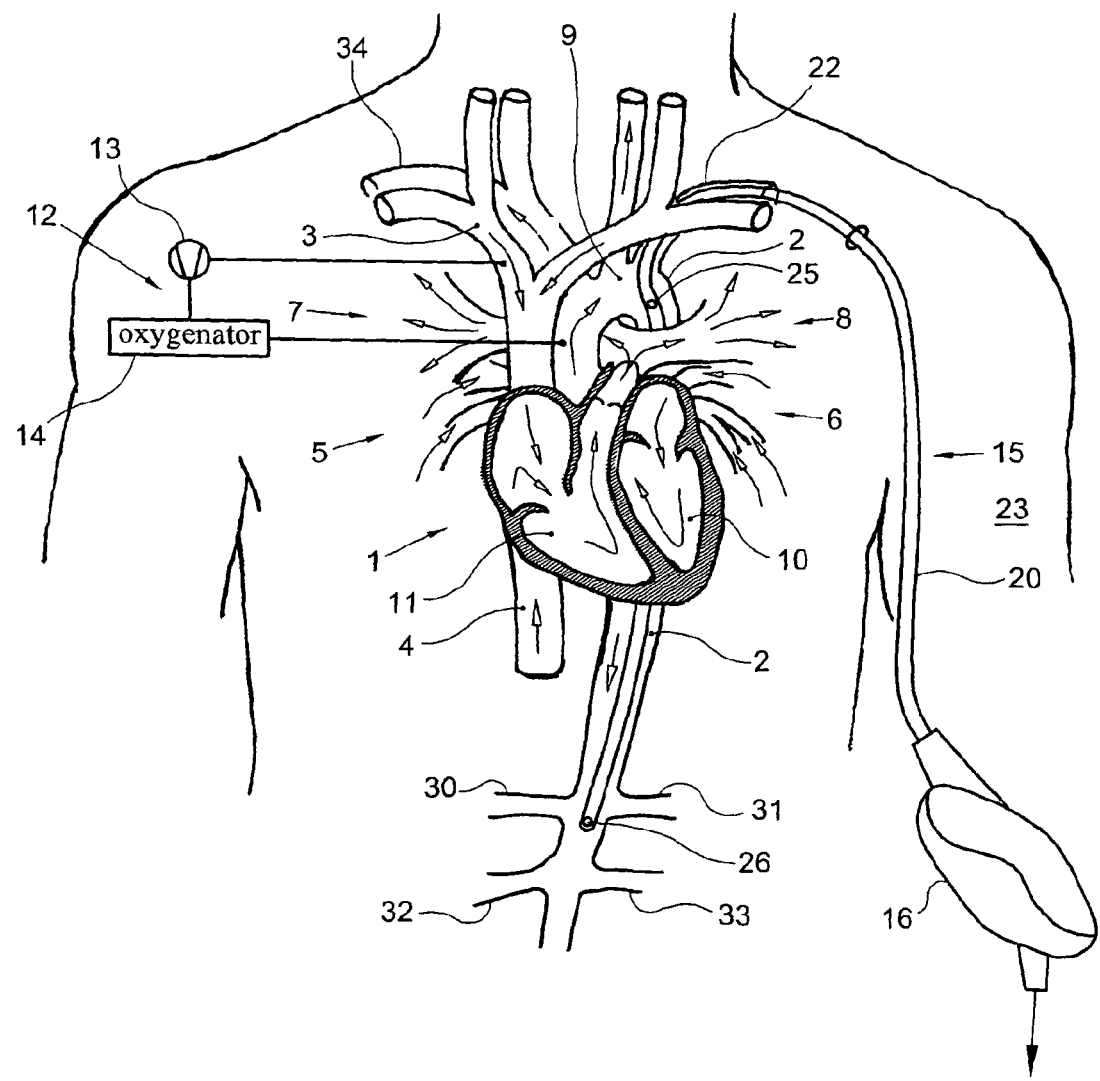
FIGS. 1 and 2 are partially cut-away views of a human thorax illustrating methods according to the invention in which examples of catheter pumps according to the invention are used.

In FIG. 1 a human thorax is illustrated in a view showing the heart 1, the aorta 2, the superior vena cava 3, the inferior vena cava 4, the right pulmonary veins 5, the left pulmonary veins 6, right pulmonary arteries 7, the left pulmonary arteries 8, the aortic arch 9, the left ventricle 10 and the right ventricle 11. Arrows indicate blood flow directions when the heart 1 is in operation. During open-heart surgery on an inactive heart 1, in practice, blood circulation is usually maintained using a heart lung machine 12 (shown schematically only) including a pump 13 and an oxygenator 14. The heart lung machine is connected to the human body for pumping blood from the vena cava 3 to the aorta 2 and maintains the blood circulation in the patient. The blood flow from the heart lung machine 12 to the patient is essentially non-pulsatile. This essentially non-pulsatile blood flow enters the aorta 2 closely adjacent the heart 1, which has been deactivated. The pump 13 is a non-pulsatile pump, which provides advantages in terms of design and compatibility with the function of the oxygenator (Allen et al.; "The importance of Pulsatile and Nonpulsatile Flow in the Design of Blood Pumps"; Artificial Organs 21(8): 922-928).

Organ failure after open-heart surgery is a frequent cause of complications. Different theories regarding the causes of such organ failure exist. One of these theories is, that the use of a heart-lung machine has several side effects that may influence blood pressure and organ perfusion. For example, the heart-lung machine causes a non-physiological (non-pulsatile flow pattern and a decreased blood viscosity when the priming liquid from the tubing and the oxygenator is introduced into the patient's blood circulation. Other instances when reduced blood pressure may disturb organ functions are during toxic shock, which may for instance be caused by an allergic reaction and, prolonged cardiac malfunction, which frequently entails multi-organ failure.

Several research results indicate that a pulsatile flow is advantageous for obtaining sufficient blood flow to the organs. For instance, pulsatile flow in a cardio pulmonary bypass has been found to have a positive effect on the blood flow rate to the kidneys of neonate pigs (Lodge et al.; "Regional Blood Flow During Pulsatile Cardiopulmonary Bypass and After Circulatory Arrest in an Infant Model"; Ann Thorac Surg 1997; 63:1243-50).

During an acute heart attack of a pig, blood flow to the liver and to the kidneys and microcirculation at cellular level were found to be improved if during three hour biventricular cardiac assist, the flow was pulsatile (Sezai et al.; "Major Organ Function Under Mechanical Support: Comparative Studies of Pulsatile and Nonpulsatile Circulation"; Artificial Organs 1999; 23(3): 280-285). During left ventricle cardiac assist in a similar situation, pulsatile cardiac assist provided superior circulation in the liver and superior microcirculation on a cellular level, at least in the initial phase of the treatment after the heart attack.

During open-heart surgery on neonate pigs, a positive effect of pulsatile flow on the blood flow to the organs, the brain and the heart muscles was found (Ündar et al.; "Effects of Perfusion Mode on Regional and Global Organ Blood Flow in a Neonatal Piglet Model"; Ann Thorac Surg; 68: 1336-43).

In clinical cardiopulmonary bypass cases, the results of measurement of cytokine, endothelium and other metabolic parameters indicated that the damage to the endothelium was less and the cytokine activation was reduced in a patient group treated with a pulsatile flow compared with another group treated with a non pulsatile flow (Orime Y. et al., "Cytokine and Endothelial Damage in Pulsatile and Nonpulsatile Cardiopulmonary Bypass"; Artificial Organs 1999; 23(6):508-512).

In FIG. 1, clinical use of a catheter pump 15 for causing the blood pressure pulsations in the aorta 2 is illustrated. The pulsatile catheter pump 15 (which is shown in more detail in FIGS. 5, 6, 13 and 14) has a displacement structure 16 in the form of a rigid housing 17 enclosing a chamber 18 divided by a flexible membrane 19. The catheter pump 15 further has a catheter 20 projecting from that displacement structure 16 and bounding a channel 36 that extends longitudinally inside the catheter for leading fluid on longitudinal direction of the catheter. The channel 36 communicates with a portion of the chamber 18 on a distal side of the membrane 19. A portion of the chamber 18 on a proximal side of the membrane 19 communicates with a sleeve 21 for connection to a pneumatic conduit communicating with a pump drive system (not shown). The displacement structure 16 can be driven via the pneumatic conduit for alternatingly applying suction for displacing fluid from the distal portion 24 of the catheter 20 to the displacement structure 16 via the channel 36 and for applying pressure for displacing fluid from the displacement structure 16 to the catheter 20, thus driving a flow through the catheter 20 which reverses in a pulsating manner.

The catheter 20 projects from the displacement structure 16 into the aorta 2 via the left subclavian artery 22 leading to the left arm 23 and is inserted into the aorta 2 of a patient in a position having its distal end portion 24 in the aorta 2 of the patient.

The distal end portion 24 of the catheter 20 is provided with inlet passages 25 arranged in a fitting 28 of the catheter 20. Spaced in distal direction from the inlet passages 25, the catheter 20 has an outlet passage 26. According to the present example, the outlet passage is arranged in a catheter tip fitting 27.

The displacement structure 16 is connected to a proximal end 29 of the catheter 20 and alternatingly withdraws blood from the aorta 2 and feeds blood to the aorta 2 via the catheter 20, such that pressure pulsations are generated in the area of the distal end portion 24 of the catheter 20. The displacement structure 16 preferably has a stroke of 10-40 ml and is preferably constructed from a transparent polymer such as PC, PMMA or MEBS. For driving the displacement structure 16 a commercially available drive system can be employed, for instance a conventional balloon pump. The displacement structure has a stroke volume which is substantially constant.

In the use of the catheter pump shown in FIG. 1, pulsations are generated in the blood flow in the aorta 2. Blood is pumped into the catheter 20 via the inlet passages 25 located in the aortic arch 9 and pumped out of the catheter 20 via the outlet passage 26 in a descending section of the aorta 2 in close proximity of arteries 30-33 towards the bowels, the liver and the kidneys.

The pulsations in the blood pressure pass into the arteries 30-33 towards the bowels, the liver and the kidneys. Such local blood pressure pulsations have a positive effect on the organ perfusion (for instance expressed as a flow rate per unit of mass of organ tissue), which is believed to be caused by increased effective organ perfusion pressure differentials. Because the pulsations are introduced in a section of the aorta 2 where its cross-section is relatively small and in close proximity of the arteries 30-33 towards the bowels, the liver and the kidneys the aorta, the magnitude of the pulsatile blood pressure peaks is relatively large in the area of the arteries 30-33 towards the abdominal organs where the pulsating effect is desired. The outflow opening 25 is preferably located between the junctions where arteries 30-33 towards the organs connect to the aorta, when the catheter is in its operating position inserted in a patient.

Moreover, since the pulsations are generated in the aorta 2, i.e. in an area downstream of and remote from the oxygenator 14, the pulsations do not interfere significantly with the operation of the oxygenator 14.

The inlet passages 25 are located upstream of the outlet passages 26, in a section of the aorta 2 that is wider than the section of the aorta 2 where the outlet passage 26 is located, so that blood can flow to the inlet passages 25 relatively easily. Moreover, this provides the advantage that the pressure reduction during intake of blood occurs at a distance upstream of the arteries 30-33 leading to the organs, so that it has relatively little influence on reducing blood flow towards the organs, while the peak pressures of the pulsations are applied closely adjacent the arteries 30-33 leading to the organs. Furthermore, the pulsations involve displacement of blood along the aorta 2, so that the reduction of its cross-section available for blood flow due to the presence of the catheter 20 is at least partially compensated by blood transport through the catheter 20. It is observed that the intake of blood may also take place outside the aorta, for instance form a buffer reservoir communicating with an outflow canula of the heart lung machine.

The spacing between the inlet passages 25 and the outlet passage 26 is preferably at least 8 cm and more preferably at least 13 cm and preferably at most 25 cm and more preferably at most 20 cm.

More in particular, the inlet passages 25 are located downstream of a section of the aorta 2 where the subclavian arteries 22, 34 connect to the aorta 2. This provides a particularly positive control over the pulsations in the arteries 30-33 towards the organs.

Because the catheter 20 is inserted into the aorta 2 via a subclavian artery 22, it can be manipulated relatively easily and from a position near the thorax of a patient that can be reached relatively easy during thorax surgery.

Figure 2:
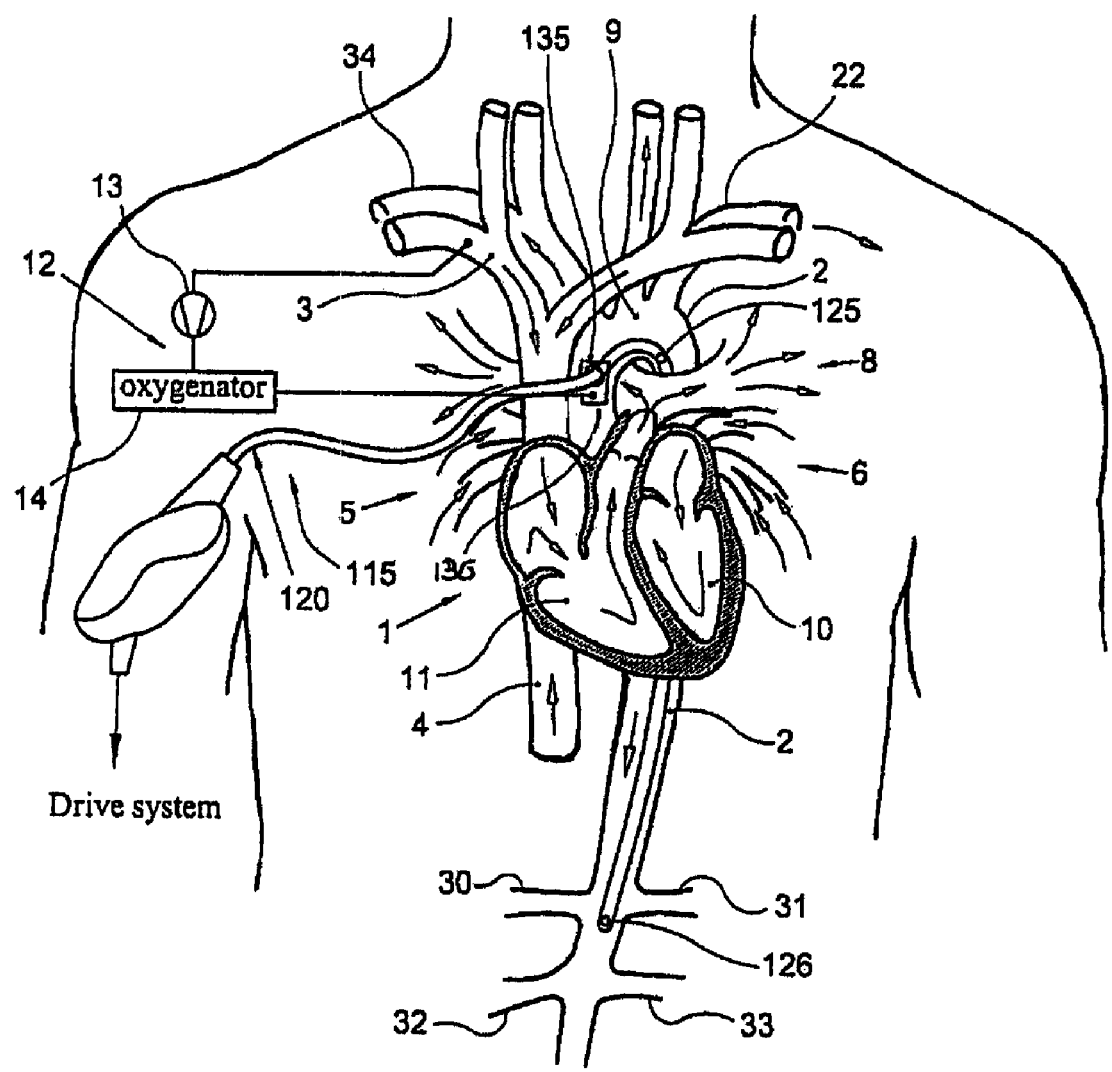

In FIG. 2, an example of a similar method according to the invention in which another example of a catheter pump 115 according to the invention used is shown. The catheter 120 is inserted into the aorta 2 via an incision 135 in the aorta 2. This provides the advantage that no further wounds have to be made in the patient's skin, that the need of guiding a catheter through an artery over a substantial distance is avoided, that a relatively short catheter can be used and that the position where the catheter 20 enters the aorta 2, is easily reached during open-heart surgery.

The catheter 120 is equipped with a fitting 136 that seals off the catheter 120 against the incision 135. To avoid the need of making a separate incision for inserting the catheter, an outflow canula of the heart-lung machine 12 may enter into the aorta via the same incision, for instance by providing that the fitting 136 seals off the catheter of the catheter pump and the outflow canula of the heart-lung machine against the same incision.

In both the clinical applications illustrated by FIGS. 1 and 2, the distal end of the catheter 20, 120 is oriented in downstream direction of the aorta and the pulsatile blood intake takes place upstream of the pulsatile blood outflow.

To provide on the one hand a sufficiently large cross-section for fluid displacement through the catheter, while on the other hand allowing easy insertion of the catheter and sufficient remaining room for blood flow through the aorta 2 or through the artery 22 through which the catheter 20 is inserted, the catheter 20 preferably has an external diameter of at least 4-5 mm and at most 6-7 mm. The optimal diameter will vary from patient to patient.

The catheter 20 has a filament (e.g. fiber or wire) reinforced wall having a thickness of 0.2 to 0.5 mm. This small wall thickness is advantageous for obtaining a large internal cross-sectional area of the catheter channel 36 combined with a small outer cross-sectional area for easy entry of the catheter 20 while the fiber reinforcement provides sufficient stiffness for easy insertion and effective pressure pulse transfer from the displacement structure 16 to the outlet passage 26.

The drive structure including the displacement structure 16 and the drive system for driving the displacement structure 16 and the catheter are preferably adapted for generating a maximum drive pressure of at least 300 mmHg and preferably at least 400 mmHg and at most about 600 mmHg. At such pressures, sufficient flow is generated to create effective pulsations while blood cell damage due to excessive shear stresses are avoided.

It is observed that in the examples according to FIGS. 1 and 2, the catheter is shown in a treatment involving the deactivation of the heart and use of a heart lung machine. However, the proposed treatment using the proposed catheter and catheter pump can also be applied advantageously for the treatment of other medical indications such as during and after heart-lung machine assist (for instance in an intensive care unit), during open heart surgery in which the heart is not deactivated and/or during periods of unwanted hypotension (shock).

Figure 3:
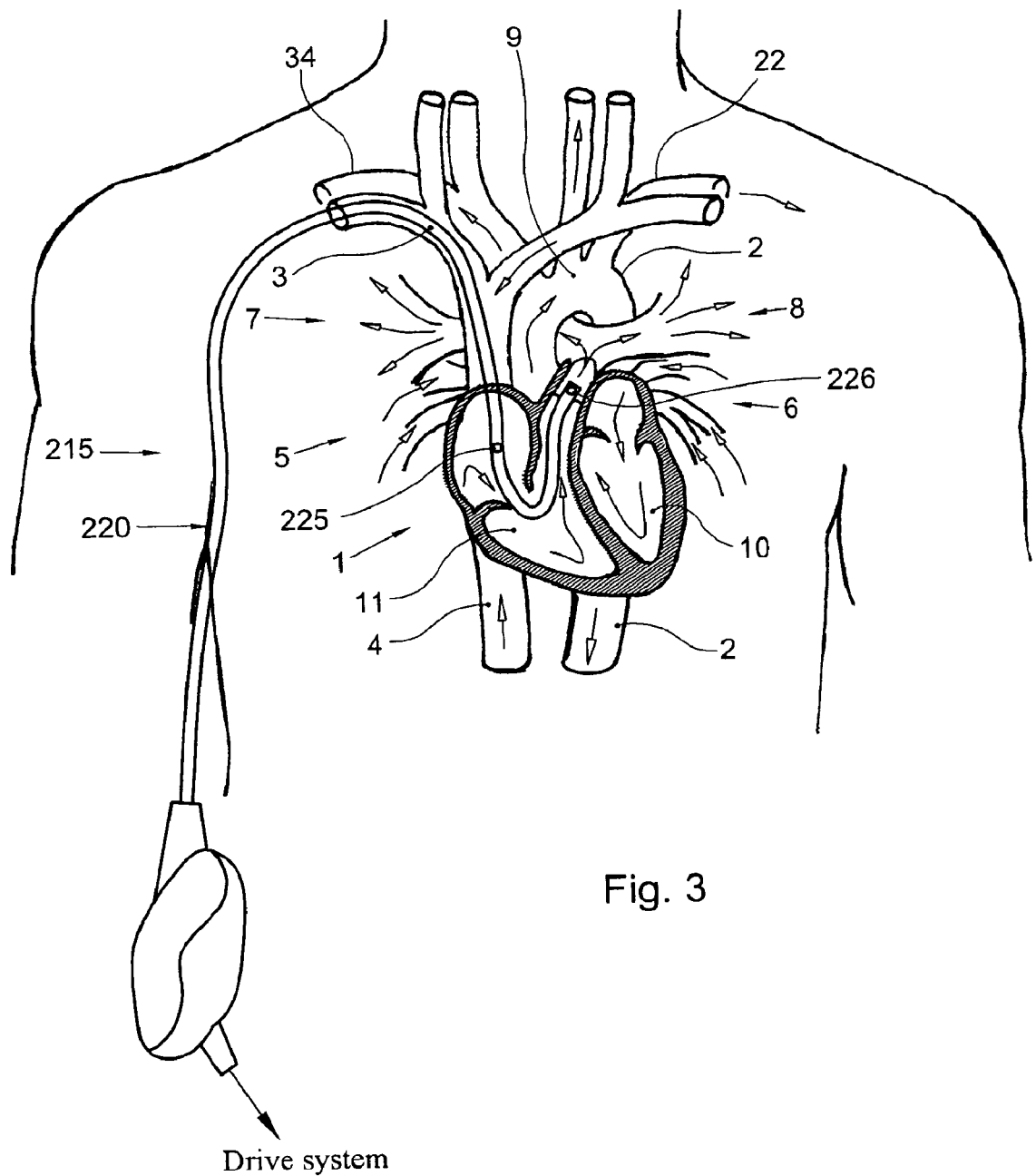
FIGS. 3 and 4 view according to FIGS. 1 and 2 are illustrating two other methods in which examples of catheter pumps according to the invention are used.

FIG. 3 illustrates another example of a further use of yet another example of a catheter pump 215 according to the invention. According to this example, the catheter pump 215 is used as a right ventricular assist device (RVAD). In such clinical use, the catheter 220 is passed through the superior vena cava 3 and through the right ventricle 11 until the outlet passage 226 is located just downstream of the right ventricle 11. The inlet passages 225 are preferably located in the right ventricle 11, so that the discharge of blood from the right ventricle is supported, but may also be located upstream of the right ventricle 11.

Figure 4:
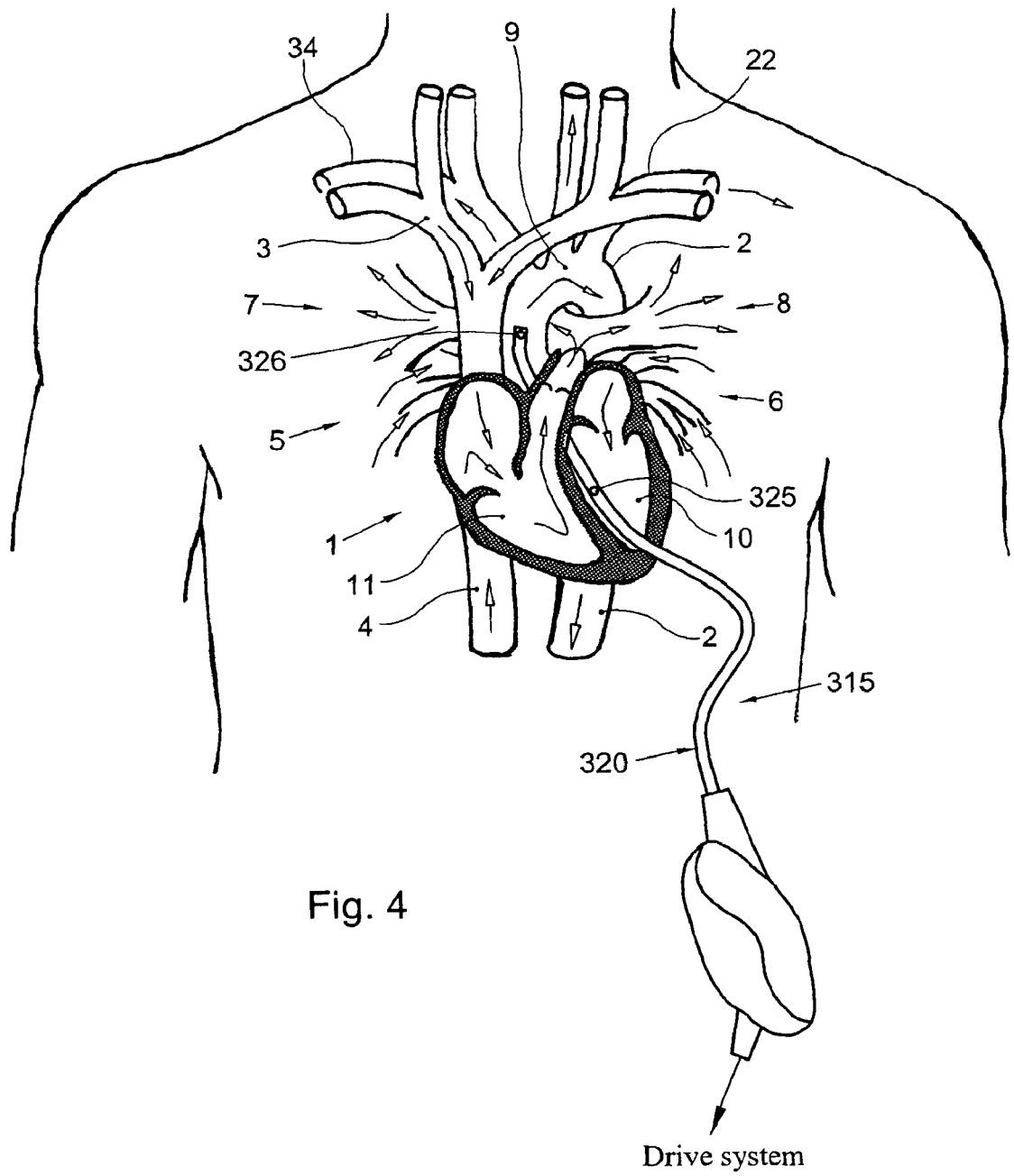

FIG. 4 illustrates yet another clinical use of yet another example of a catheter pump 315. According to this example, the catheter pump 315 is used as a left ventricular assist device. In this clinical use, the catheter 320 is passed through an incision in a wall portion of the left ventricle 10 and through the left ventricle 10 until the outlet passage 326 is located just downstream of the right ventricle 11. The inlet passages 325 are preferably located in the left ventricle 10, so that the discharge of blood from the left ventricle 10 is supported, but may also be located upstream of the left ventricle 10.

In the present examples, the fluid that is displaced to and from in the catheter is blood from the patient. In principle, it is also possible to transfer the pulsations applied by the displacement structure 16 using another fluid such as air or a liquid. The displacement structure may also be provided in another suitable form, such as for example in the form of a piston in a cylinder or of a bellows.

Figure 5:
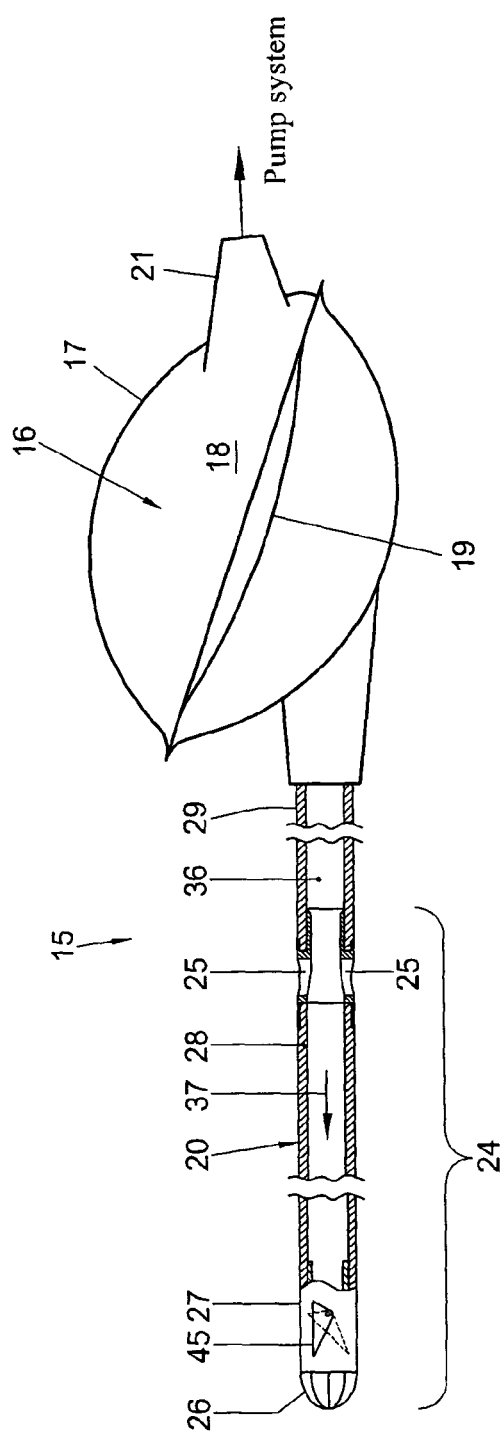
FIG. 5 is a side view, partially in longitudinal cross-section of an example of a catheter pump according to the invention.
Figure 6:
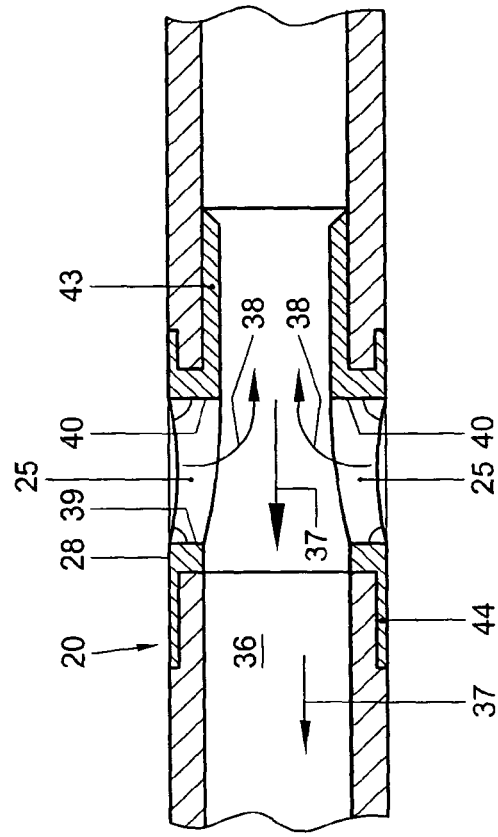
FIG. 6 is a side view in cross-section of an inlet section of the catheter according to FIG. 5.
Figure 7:
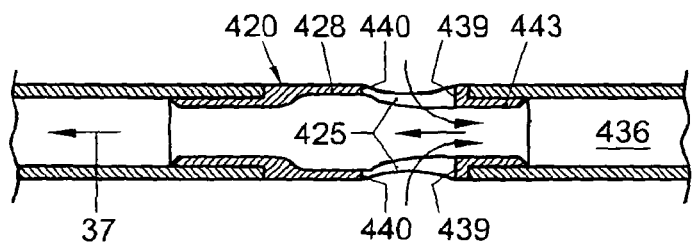
FIG. 7-12 are enlarged views in cross-section of inlet sections of other examples of catheter pumps according to the invention.

The fitting 28 in which the inlet passages 25 are located and adjacent sections of the catheter 20 are shown in more detail in FIG. 6. The fitting catheter tip 27 in which the outlet passage is located is shown in more detail in FIGS. 13 and 14. The catheter pump, the catheter and the fittings as shown in FIGS. 1, 5, 6, 12 and 14 represent the presently most preferred embodiment of the invention.

The fitting 28 forms an inlet tube in which inlet passages 25 are arranged. According to this example, the inlet tube fitting 28 has a circular cross-section, but other cross-sectional shapes are conceivable as well.

In operation, blood that is urged by the displacement structure in distal direction (arrow 37) is jetted out of a section of the channel 36 immediately proximally of the inlet passages 25, mainly or completely past the inlet passages 25 and into a section of the channel 36 immediately distally of the inlet passages 25. Because the sections of the channel 36 immediately distally and proximally of the inlet passages 25 are in-line with each other, very little or no blood is urged out of the inlet passages 25, in spite of the inlet passages 25 being continuously open.

When the displacement structure 16 is reversed and pulls blood in proximal direction, blood flow is not specifically directed from the channel section immediately distally of the inlet passages 25, but is, at least to a large extent, attracted via the inlet passages as is indicated by arrows 38.

Thus, the net result of the alternating displacement of blood through the channel 36 by the displacement structure is, that during each cycle at least more blood is displaced from the inlet passages 25 towards and out of the outlet passage 26 than from the outlet passage 26 to the inlet passages, even if no valve is arranged between the inlet passages 25 and the outlet passage 26.

Because blood flow through the inlet passages 25 may be controlled without moving valve bodies, a simple and therefore reliable operation is achieved and the risk of thrombosis and causing damage to the blood cells normally associated to moving valve bodies in blood pumps are avoided.

Figure 11:
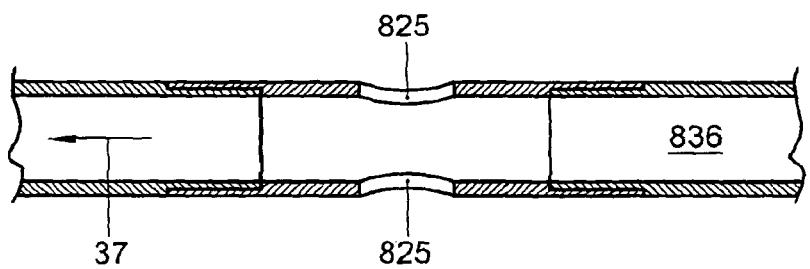

Several features may be provided for improving the net blood displacement per cycle in distal direction. However, depending on the clinical application, for instance a channel 836 as shown in FIG. 11 having a constant cross-section from a proximal side of the inlet passages 825 to a distal side of the inlet passages 825 may be sufficiently effective. The inlet passages may also be provided directly in a wall of catheter tubing, although providing the inlet passage or passages in an inlet tube fitting generally allows more freedom of design an a more accurate finish. Supply tubes may connect to the inlet passages. In each embodiment, a single inlet passage or a larger number of inlet passages may in principle be provided. In each of FIG. 6-12 an arrow 37 indicates the distal direction.

In the embodiments shown in FIGS. 6-8 and 10, a section of the channel 36; 436; 536; 736 immediately distally adjacent the inlet passages 25; 425; 525; 725 is wider than a section of the channel 36; 436; 536; 736 immediately proximally adjacent the inlet passages 25; 425; 525; 725. With this feature, a partial vacuum is generated at the inlet passages 25; 425; 525; 725, when a blood flow in distal direction is passed through the channel, so that outflow of blood via the inlet passages 25; 425; 525; 725 is at least counteracted and blood may even be caused to be drawn into the channel via the inlet passages 25; 425; 525; 725 during the stroke of the displacement structure 16 in distal direction.

Throughput of the catheter pump in distal direction may also be improved by providing that, as in FIG. 6-9, at least a portion of an inlet section of the channel 36; 436; 536; 636 between most upstream and most downstream boundaries 39, 40; 439, 440; 539, 540; 639, 640 of the inlet passages 25; 425; 525; 625 is narrower than sections of the channel 36; 436; 536; 636 distally and proximally adjacent the inlet section. Thus a construction of the channel causing a venturi effect is achieved.

In the embodiments shown in FIGS. 6-8 and 10, an inlet section of the channel 36; 436; 536; 736 between most upstream and most downstream boundaries 39, 40; 439, 440; 539, 540; 739, 740 of the inlet passages 25; 425; 525; 725 widens in distal direction from a narrowest section of the channel 36; 436; 536; 736 immediately upstream of the inlet section, so that the blood flow in distal direction is guided in a direction from which the inlet passages diverge, until immediately upstream of the inlet passages, so that the flow is effectively kept away from the inlet passages.

Figure 8:
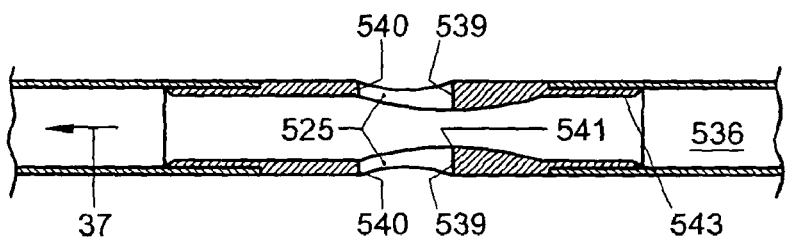
Figure 9:
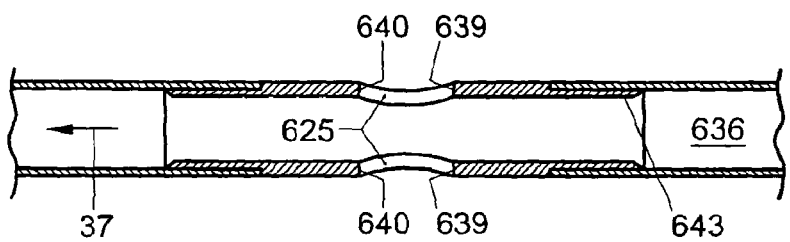
Figure 10:
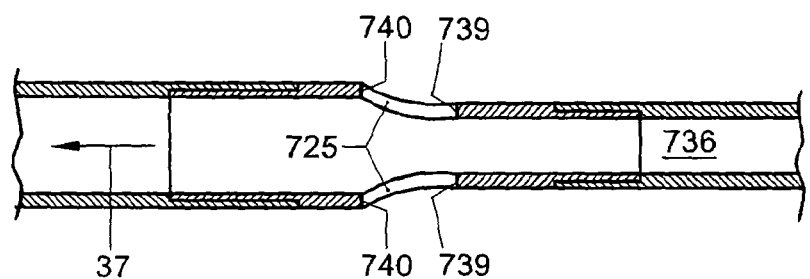

In the embodiment shown in FIG. 8, moreover, a section of the channel 536 proximally adjacent the inlet passages 525 gradually tapers in distal direction to a narrowest cross-section and an apex 541 closely proximal of the inlet passages 525 forms a transition between the gradually narrowing and widening channel sections. This causes blood flowing in distal direction 37 to converge away from the inlet passages 525, at least over some distance along the inlet passages 525.

Figure 12:
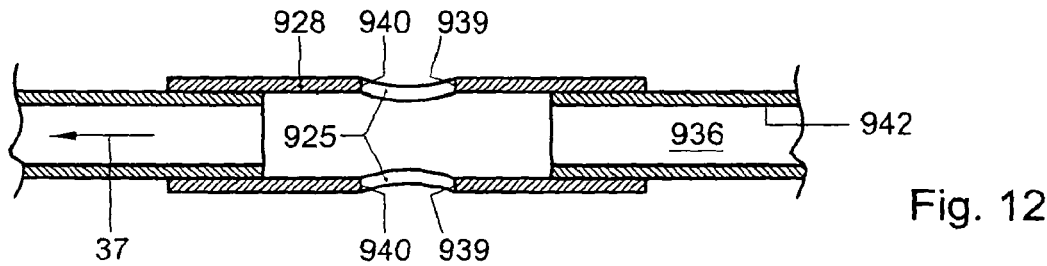

In the embodiment shown in FIG. 12, an inlet section of the channel 936 between most upstream and most downstream boundaries 939, 940 of the inlet passages 925 is recessed relative to an interior surface 942 of a catheter wall section 942 closely proximal of the inlet passages 925. This also contributes to keeping the blood flow is distal direction away from the inlet passages 925. In the embodiment according to FIG. 12, the recessed channel section containing the inlet passages 925 is achieved in a simple manner by providing the inlet passages 925 in a portion of the inlet tube fitting 928 and arranging the catheter tubing connected to the inlet fitting 928 inside the inlet tube 928.

In the embodiments shown in FIG. 6-9, at least a proximal end portion of the inlet tube fitting 28; 428; 528; 628 includes a sleeve 43; 443; 543; 643. A section of catheter tubing proximal of the inlet passages 25; 425; 525; 625 is mounted over the sleeve 43; 443; 543; 643 and a section of the channel 36; 436; 536; 636 inside the sleeve 43; 443; 543; 643 is narrower than at least one adjacent section of the channel 36; 436; 536; 636. Thus, an efficient construction is obtained, because the construction of the channel upstream of the inlet passages also forms the sleeve for receiving catheter tubing connected to the inlet tube fitting.

In the embodiment according to FIG. 6, the catheter tubing at the distal side of the inlet tube fitting 28 is arranged inside a sleeve 44 at a distal side of the inlet tube fitting 28. This allows to injection mould the inlet tube fitting 28 more easily, since the internal cross-section of the channel only stays equal or widens in distal direction 37. Moreover, a relatively wide channel section is obtained distally of the inlet passages 25, because no sleeve constricts the internal cross section of the channel inside the catheter tubing distally of the inlet passages 25.

To further reduce the risk of blood damage and thrombosis and to further simplify the design of the catheter pump, it is advantageous if, at least in operating condition, the channel 36 is free from valves between the inlet passages 25 and the outlet passage 26. This is particularly advantageous in applications in which the main purpose of the catheter is to generate pulsatile blood pressure for improving organ perfusion.

However, in particular in applications as shown in FIGS. 3 and 4, in which the catheter extends through a ventricular valve of an active heart, it has been found to be advantageous to provide a check valve with a movable valve body 45 between the inlet passages and the outlet passage, for instance as is shown in FIG. 5, to avoid creating a substantial open passage across a ventricular valve.

Figure 13:
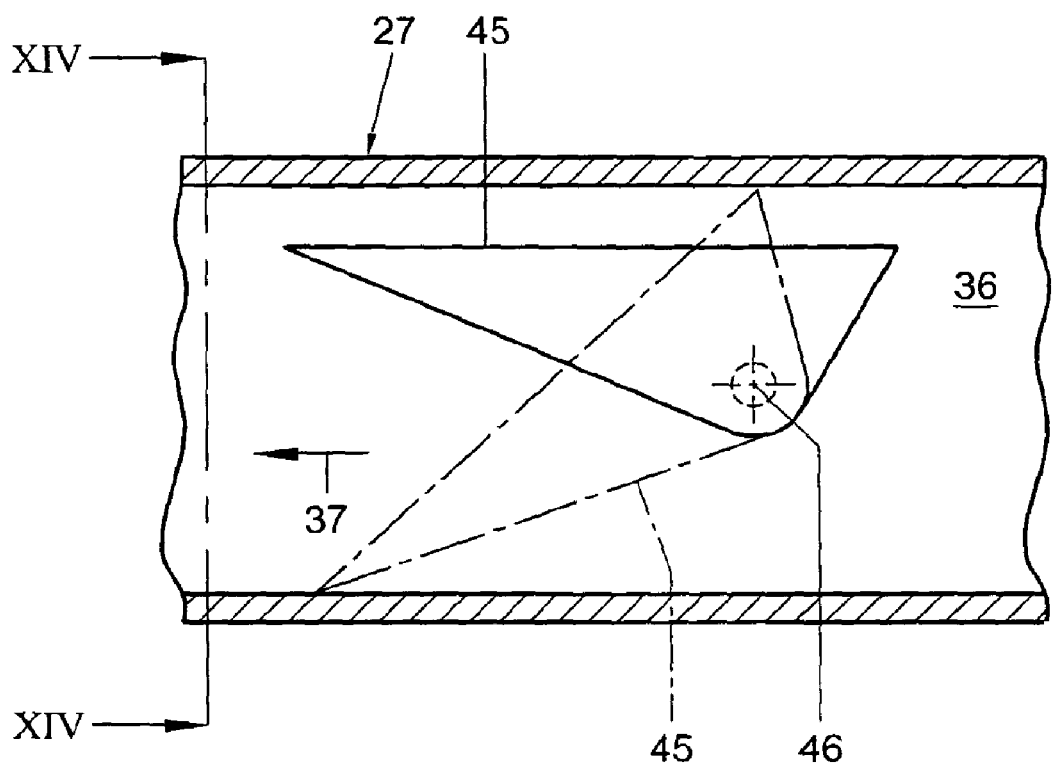
FIG. 13 is a side view in cross-section of a section of the catheter according to FIG. 5 where a one-way valve is located.
Figure 14:
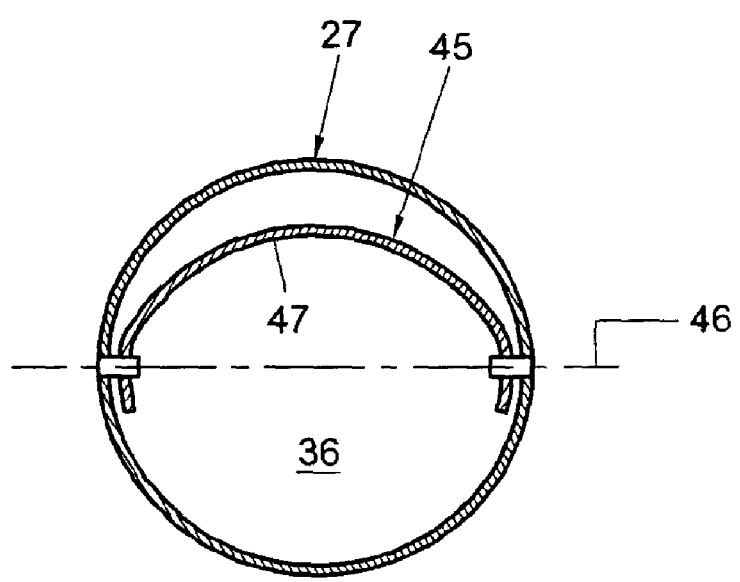
FIG. 14 is a view in cross-section along the line XIV-XIV in FIG. 13.

According to the example shown in more detail in FIGS. 13 and 14, the valve body 45 pivotably suspended for rotation about an axis 46 extending across the channel 36, between a closed position (shown in dash-and-dot lines), substantially closing off the channel 36 and an open position (shown in full lines and in FIG. 14) allowing fluid to pass past the valve body 45. In open position, the valve body 45 extends along a plane parallel to the channel 36 and, in axial view, has a central portion 47 spaced from the pivoting axis 46 and, in side view, the valve body projects from the pivoting axis further in distal direction than in proximal direction.

Starting from a closed position of the valve body 45, since (at least in open condition) the valve body 45 projects from the pivoting axis 46 further in distal direction than in proximal direction, blood pressure in distal direction 37 results in the exertion of a couple on the valve body 45 which causes it to pivot to its open position and it is held in that position by the blood flow in distal direction 37. After the stroke of the displacement structure 16 urging blood in distal direction has ended, the displacement structure 16 starts to draw blood in proximal direction. Already a small backflow at the valve body resulting from the reversal of the action of the displacement structure 45 causes the valve body 45 to pivot back to its closed position. Initial movement of the valve body 45 is believed to be caused by a difference in flow velocities between the centre and the periphery of the channel 36. As soon as the valve body is tilted a little in closing sense, the flow pushes against the surface of the valve body 45 facing away from the axis 46, which causes the valve body to be pivoted into its closed position, blocking any substantial backflow.

Because, in open position, the valve body 45 extends along a plane parallel to the channel 36 and, in axial view, has a central portion 47 spaced from the pivoting axis 46, the valve 45 leaves open a large portion of the lumen of the catheter for the passage of tools and causes very little resistance to the blood flow. Furthermore, opening and closing of the valve 45 does not require any material to bend, which is advantageous for obtaining reliable operation over prolonged periods of time.

For closing off the channel 36, which has a round cross-section, it is advantageous that the pivoting axis 46 extends across a widest portion of the channel 36 (measured in the direction of the axis), because this allows the valve body 45 to be wide enough to close off the channel along the entire circumference of the channel 36, while still allowing pivotal movement about the axis 46 between the closed and open positions.

Moreover, it is made possible that, as in the present example, a section of the channel 36 containing the valve body 45 has a constant cross-section so that flow resistance is minimized, while nevertheless, the valve body 45 in closed condition substantially abuts the continuing interior wall surface of the channel 36 along the entire circumference of the channel 36.

According to the present example, the valve body 45 is a curved plate. In open position, the valve body 45 leaves open passages between the plate and the catheter wall on both sides of the plate, so that blood can flow past the plate on both sides, which is favourable for avoiding areas of little flow where the risk of thrombosis is increased. The space between the plate and the interior wall of the channel 36 when the plate is in open position also allows the plate to pivot to its closed position.

According to the present example, the valve fitting 27 also forms a distal tip of the catheter 20. It is, however, also possible to position the valve fitting more proximally or to integrate the valve in the inlet tube fitting.

The fittings 22, 28 may be coupled to catheter tubing in a manner as is described in International patent application WO 97/18936.

What is claimed is:

1. A catheter pump comprising:
a catheter comprising:
a catheter wall bounding a channel inside said catheter;
a distal end portion;
a proximal end portion, said proximal end portion communicating with said distal end portion via said channel;
at least one inlet passage in said wall; and
at least one outlet passage for allowing fluid to flow out of said channel, said outlet passage being located distally from and spaced from said inlet passage; and
a displacement structure dimensioned and configured for, while in operation, alternatingly applying suction and pressure for cyclically driving fluid displacement through said channel in a direction away from said distal end portion towards said proximal end portion and in a direction away from said proximal end portion towards said distal end portion, said catheter projecting distally from said displacement structure and said channel communicating with said displacement structure;
wherein, at least in operating condition, said at least one inlet passage is continuously open, and
wherein the channel, the inlet passage and the outlet passage are arranged such that over a complete cycle of the fluid displacement in said channel towards and away from said proximal end portion, a net displacement of blood from the inlet through the channel to the outlet is obtained; the distal end portion of the catheter being dimensioned and configured to extend into a patient's heart or into an artery of a patient; and the inlet passage and the outlet passage being inlet and outlet passages of a single lumen.

2. A catheter pump according to claim 1, wherein a section of said channel distally adjacent said at least one inlet passage is wider than a section of said channel proximally adjacent said at least one inlet passage.

3. A catheter pump according to claim 1, wherein at least a portion of an inlet section of said channel between most proximal and most distal boundaries of said at least one inlet passage is narrower than sections of said channel distally and proximally adjacent said inlet section.

4. A catheter pump according to claim 1,
wherein an inlet section of said channel between most proximal and most distal boundaries of said at least one inlet passage widens in distal direction from a narrowest section of said channel immediately proximal of said inlet section, and
wherein a section of said channel proximally adjacent said at least one inlet passage gradually tapers in distal direction to a narrowest cross-section and wherein an apex closely proximal of said at least one inlet passage forms a transition between said gradually narrowing and widening channel sections.

5. A catheter pump according to claim 1, wherein an inlet section of said channel between most proximal and most distal boundaries of said at least one inlet passage is recessed relative to an interior surface of said catheter wall closely proximal of said at least one inlet passage.

6. A catheter pump according to claim 1, wherein said catheter includes at least one inlet tube fitting, said at least one inlet passage being arranged in a catheter wall portion of said inlet tube fitting.

7. A catheter pump according to claim 6, wherein at least a proximal end portion of said inlet tube fitting includes a sleeve, a section of said catheter proximal of said at least one inlet passage being mounted over said sleeve and a section of said channel inside said sleeve being narrower than at least one adjacent section of said channel.

8. A catheter pump according to claim 1, wherein
said outlet passage is located distally from and spaced at least 8 cm from said inlet passage.

9. A catheter pump according to claim 1, wherein the displacement structure is arranged for alternatingly generating suction and pressure pulsations.

10. A catheter pump according to claim 9, wherein the displacement structure has a stroke volume which is substantially constant.

11. A catheter pump according to claim 1, wherein
the displacement structure is in the form of a rigid housing enclosing a chamber divided by a flexible membrane, a portion of the chamber on a distal side of the membrane communicating with the channel inside said catheter and a portion of the chamber on a proximal side of the membrane communicating with a connection for a pneumatic conduit, for, via the membrane, alternatingly applying the suction and the pressure for cyclically driving the fluid displacement through said channel.

* * * * *